(12) United States Patent
Scherer et al.

(10) Patent No.: US 9,415,133 B2
(45) Date of Patent: Aug. 16, 2016

(54) HYDROGEL

(71) Applicant: Euro-Celtique S.A., Luxembourg (LU)

(72) Inventors: Sabine Scherer, Limburg-Dietkirchen (DE); Christian Wagner, Gemuenden (DE); Christian Leuner, Frankfurt (DE); Wolfgang Fleischer, Ingelheim (DE)

(73) Assignee: Euro-Celtique S.A., Luxembourg (LU)

( * ) Notice: Subject to any disclaimer, the term of this patent is extended or adjusted under 35 U.S.C. 154(b) by 0 days.

(21) Appl. No.: 14/057,995

(22) Filed: Oct. 18, 2013

(65) Prior Publication Data
US 2014/0141063 A1 May 22, 2014

Related U.S. Application Data

(63) Continuation of application No. 13/733,829, filed on Jan. 3, 2013, now abandoned, which is a continuation of application No. 12/278,036, filed as application No. PCT/EP2007/000824 on Jan. 31, 2007, now abandoned.

(30) Foreign Application Priority Data

Feb. 2, 2006 (EP) .................................... 06002149

(51) Int. Cl.
*A61L 15/24* (2006.01)
*A61L 15/44* (2006.01)
*A61L 26/00* (2006.01)

(52) U.S. Cl.
CPC .................. *A61L 15/24* (2013.01); *A61L 15/44* (2013.01); *A61L 26/008* (2013.01); *A61L 26/0014* (2013.01)

(58) Field of Classification Search
CPC ... A61L 26/0014; A61L 15/24; A61L 26/008; C08L 33/02
USPC .......... 242/445, 485, 487, 488, 450, 667, 719
See application file for complete search history.

(56) References Cited

FOREIGN PATENT DOCUMENTS

| EP | WO 2004/073682 | * | 9/2004 | ............. A61K 9/127 |
| WO | WO 02/17979 | * | 3/2002 | ............. A61L 15/500 |

OTHER PUBLICATIONS

Lubrizol. Carbopol 980 NF Polymer (Jun. 14, 2007).*

* cited by examiner

*Primary Examiner* — Anna Falkowitz
(74) *Attorney, Agent, or Firm* — Dechert LLP

(57) ABSTRACT

The invention is related to gel preparations capable of absorbing as well as releasing liquid, and the use of such gel preparations in the treatment of wounds.

19 Claims, No Drawings

HYDROGEL

CROSS REFERENCE TO RELATED APPLICATIONS

This application is a continuation of application Ser. No. 13/733,829, filed Jan. 3, 2013, which is a continuation of application Ser. No. 12/278,036, filed Sep. 23, 2008, which is a national stage entry of International Application No. PCT/EP07/00824,filed Jan. 31, 2007, which claims priority under 35 U.S.C. §§119(a)-(d) and 365(b) to European patent application no. 06002149.0, filed Feb. 2, 2006, the contents of all of which are incorporated herein by reference.

The present invention is related to gel preparations capable of absorbing as well as releasing liquid, and the use of such gel preparations in the treatment of wounds.

The damage of body tissue can have a variety of causes. Wounds can be caused e.g. by (mechanical) contact of weapons, tools, vehicles or other objects with the human or animal body. Furthermore, serious damage of the skin can also be caused by exposure to heat, cold or radiation as well as by contact with aggressive chemicals. Body tissue can of course be damaged or even destroyed by infective diseases, caused e.g. by microorganisms or viruses.

Once damage of body tissue has occurred, the body will generate new body tissue, as a main activity of the tissue repair process. However, the generation of new body tissue may sometimes have a negative effect, e.g. if the repaired or re-grown tissue does not provide the same performance characteristics than the original tissue.

Sometimes the negative effect can be solely cosmetic, in that the re-grown tissue or repaired tissue is functional, but perceived as disfiguring or unaesthetic. However, in more severe cases, the necessary functionality of the tissue may be impaired.

Thus, tissue repair can result in scar formation, which may lead to cosmetic problems, but may also render the affected body tissue less functional, e.g. less elastic. This effect is not limited to the external skin of the human or animal body; scar tissue can also lead to reduced functionality of mucosa or other body tissue, including that of internal organs of the body.

Corresponding types of undesired tissue repair effects include hyperkeratosis and unregulated proliferation of tissue.

The need for control of such effects in the treatment of diseases, wounds, burns etc. has become the object of much attention.

In the therapy of wounds, a moist wound healing environment has been shown to be often beneficial. It has been found that the survival of cells in a moist environment is improved, while a dry environment promotes the die back of cells.

During wound healing, ichor is formed, which serves to establish a liquid milieu. In addition, the ichor contains components, like amino acids, electrolytes, etc., which support the cell metabolism and thus enhance wound healing.

Within the first phase after tissue damage, eschar is generally formed to "seal" the wound.

Even though eschar protects the wound from exterior influences, it absorbs ichor and thus can cause drying of the wound, and consequently may negatively influence the conditions for wound healing.

In a moist wound healing environment, the formation of eschar is reduced or even prevented. This may create the need for alternative measures, to cover and protect the healing wound.

A further benefit of a moist wound healing environment is that it also provides a better physiological basis for new cell growth. Cell growth, which is required for wound healing, is activated and the formation of new tissue is favored in the moist wound healing environment. Some ichor formation is beneficial in this context.

However, in case the wound environment contains too much ichor, this may adversely affect the wound healing properties.

The moist wound healing environment required for wound healing is improved in particular when the liquid content within the wound is optimized by suitable substances or preparations.

A typical known method to produce a moist wound healing environment is to use a topical gel, in particular a hydrogel, in a wound dressing. These gel wound dressings are especially useful as occlusive wound dressings. In the context of the present specification the term "gel" always includes a hydrogel.

The known gels/hydrogels can be able to release liquid from the gel matrix, thus forming a suitable liquid reservoir for the wound environment. On the other hand, gels are in general also capable of absorbing liquid, e.g. ichor, from the wound, if their liquid content can be further increased and may also by this fact provide for an improved wound healing environment.

"Liquid" generally means aqueous liquids, including liquids provided by the gel manufacturer or user (e.g. aqua dest., solutions of actives, suspensions and dispersions) and also including liquids produced by or in a wound (e.g. produced by the affected tissue). "Liquid" includes liquid released by the gel and liquid (which may be different from such released liquid) re-absorbed from the wound.

Without being bound by any specific theory, it is believed that hydrogels have an additional beneficial effect on the moist wound healing environment by "binding" certain compounds or contaminations into the gel, and thus improving the conditions for healing by removal of such materials from the wound.

Another benefit of the application of gels, especially hydrogels is, that a gel layer may "seal" the wound (without drying it) and thus enables easier dressing changes. If e.g. the dressing sticks to the wound, the wound may be newly injured when the dressing is removed. If a suitable gel is covering the wound, it is possible to change the dressing without reopening the already recovered wound, or causing new injuries.

In the prior art, several types of gel-based wound healing preparations have been described. Within these preparations, various different types of gel-forming polymers have been used. These gel-forming polymers include e.g. carboxymethylcelluloses, modified starch and alginate polymers.

These prior art gels are especially discussed, in the art with respect to their capacity for absorbing liquids from the wound.

Examples of gels, which are commercially available and can be applied in wound-healing include IntraSite® Gel (available from Smith & Nephew), Askina® Gel (available from Braun) and Varihesive® Gel (available from ConvaTec). These gels exhibit good liquid absorption capabilities. Their liquid release capabilities are, however, significantly lower than their liquid absorption capacities.

The known gels can contain various additional ingredients to adapt them for their intended use. For example some of these gels comprise active agents to provide anti-inflammatory properties or the like.

The use of wound healing promoting agents in combination with antiseptic agent using liposomal preparations for external applications is e.g. disclosed in EP 0 639 373. Liposomes are highly suitable carriers for antiseptic agents, especially povidone iodine and provide an extended topical activity by interaction with cell surfaces.

Liposomes are well known drug or compound carriers and thus the application of medicaments in liposomal form has been the subject of investigation for quite some time. An overview concerning the administration of compounds in liposomal form to the skin is e.g. provided by the review "Targeted delivery to the pilosebaceous unit via liposomes", Lauer et al. (1996), Advanced Drug Delivery Reviews, 18, 311-324. This review describes the physico-chemical characterization of liposomal preparations and their therapeutic application for the treatment of the pilosebaceous unit. Compounds that have been investigated for delivery by liposomes include e.g. anti-cancer agents, peptides, enzymes, anti-asthmatic and anti-allergic compounds and also antibiotics.

Lately, it has been found that liposomal antiseptic preparations of povidone iodine can be used for the treatment of diseases of the upper and lower respiratory tract, as disclosed in WO 99/60998 and WO99/60999.

Liposomal antiseptic preparations can be used for the treatment of herpes, acne and other specific diseases of the skin, as described in WO04/073720, WO04/073682 and WO04/073683.

In addition, WO 00/72822 discloses the use of liposomal preparations comprising anti-infective and/or anti-inflammatory agents for functional and cosmetic tissue remodeling and repair treatments.

The prior art still leaves a desire for optimization of the liquid content within the wound, in particular in balancing the liquid absorption and the liquid release properties of the gel-preparations.

Therefore, it is an object of the present invention to provide a preparation with improved wound-healing properties.

It is a further object of the invention to provide preparations which exhibit improved liquid release to the wound.

It is another object of the present invention to provide a preparation wherein the capability of the hydrogel to release liquid is greater than its capability to absorb liquid from the wound.

It is a further object of the invention to use the preparation for the production of a medicament with improved wound healing properties, in particular liquid releasing properties.

According to the invention these objects are attained by the feature combinations of the independent claims.

Advantageous embodiments of the invention are defined in the dependent claims.

It has been found that the preparations according to the invention exhibit a surprisingly high capability to maintain a moisture level within the wound, which seems to be suitable to enhance wound healing. In particular, the inventive preparations are able to release moisture or liquid from the gel to maintain a suitable moisture level within the wound, and in this capacity, the inventive preparations are superior to comparable known preparations.

In preferred embodiments the preparation according to the invention reveals a liquid release capability which is greater than its liquid absorption capability. However, the liquid absorption capability of the inventive preparation is still suitable to absorb liquid from the wound, as necessary.

One aspect of the present invention provides gel preparations which can comprise active agents, in particular anti-inflammatory agents, particulate carriers, in particular liposomes, film-forming substances or combinations thereof.

In a second aspect the present invention provides gel preparations which do not contain either active agents, particulate carriers, film-forming substances or combinations thereof.

In preferred embodiments, the preparations according to the invention comprise at least one gel-forming polymer.

The gel-forming substance of the present invention can e.g. be selected from the group consisting of agar, alginates, alginic acids, Arabic gum, gelatine, starch, tragacanth gum, methylcelluloses, hydroxyethylcelluloses, carboxymethylcelluloses, polyacrylic acids and/or combinations thereof. In preferred embodiments, acrylic acid polymers are applied. Polymers complying the USP Carbomer 940 monograph like Carbopol 908NF or Carbomer 940) are preferred from this group.

In specifically preferred embodiments the gel-forming substances comprise polyacrylates, polymethacrylates, polyacrylic acids, polymethacrylic acids, polyvinylalcohols and combinations thereof. Polyacrylic acids are particularly preferred.

In preferred embodiments of the invention, gel-forming substances are used in the form of hydrogels. A hydrogel, as used in the present invention, is a gel on the basis of a hydrophilic composition or compound, which is capable of absorbing and/or releasing a certain amount of liquid, in particular water.

The pH of the preparation according to the invention is preferably generally in the range from 3 to 7, more preferably from 4 to 6.5 and even more preferably in the range from 5 to 6.

The gel-forming substance is present in the preparation according to the invention at between about 0.1% and about 10%, preferably between about 0.5% and about 5%, more preferably between about 1.0% and about 3.0%. All these percentages are wt.-%, based on total preparation weight.

In a preferred embodiment the preparation according to the invention further comprises liposomes. This often has a beneficial effect on wound-healing.

Since, however, the addition of liposomes may cause some loss of liquid release capability, it is preferred in other embodiments, to provide the inventive preparation without addition of liposomes and/or other particulate carrier materials.

The amphiphilic substances generally known in prior art to form liposome membranes can be employed in the context of the invention, as long as they are pharmaceutically acceptable for the intended application. Presently, liposome-forming systems comprising lecithin are preferred. Such systems can comprise hydrogenated soy bean lecithin, besides cholesterol and disodium succinate-hexahydrate or the like. Usually one will make sure that the liposome-forming materials do not show any unintended reactivity with any other ingredient. In case, the preparation according to the invention comprises a reactive agent, e.g. elemental iodine, higher contents of compounds with reactive groups such as double-bonds, for example high cholesterol contents, are usually avoided. It is presently specifically preferred to use hydrogenated soy bean lecithin as the sole membrane-forming agent. Commercially available products such as Phospholipon® 90 H are preferred.

As can be taken from the review of Lauer A. C. et al. 1995 (vide supra) phospholipid-based liposomes may also be generally used for production of liposomes that discharge a cargo of actives into the skin. According to this review, the use of non-ionic liposomes, which can be formed with phosphatidylcholin, is also an option. Other components that may be used for the formation of micelles are also known to the person skilled in the art and may be used for the production of preparations according to the invention.

The known prior art methods for forming liposome structures can generally be used in the context of the invention. Broadly, these methods comprise mechanical agitation of a suitable mixture containing the membrane-forming substance and water or an aqueous solution. Filtration through suitable membranes is preferred in order to form a substantially uniform liposome size.

The average size of the liposomes according to this invention can vary over a broad range, generally from about 1 μm to about 150 μm. Liposomes or particulate carriers having sizes in the range of about 1 μm and 70 μm are preferred. Generally the size of liposomes should be selected such that a good penetration into the skin is guaranteed. A particularly preferred embodiment of the invention therefore comprises liposomes having a size of between about 10-30 μm.

Additionally these preparations preferably comprise liposomes of rather large size such as liposomes having a size of between about 1 μm and 30 μm, preferably between about 10 μm and 30 μm, more preferably between 20 μm and 30 μm and most preferably at around 25 μm. The formulation as a hydrogel is preferred.

Generally, liposomes having a rather small average size are better suited for production of solutions, dispersions and suspensions. Such rather small sizes typically comprise sizes of around 1 μm to 10 μm, or even smaller in the case of solutions. In contrast, gel or ointment formulations may comprise liposome of a size of up to 50 μm.

Even though we discuss the use of liposomes in the inventive preparation, it is assumed that further particulate carrier materials known to a person skilled in the art can similarly be used. These alternative materials may be e.g. microspheres, nanoparticles, or large porous particles.

In a preferred embodiment, the preparation of the invention further comprises at least one film-forming substance.

In some cases, the addition of the film-forming substance may cause some loss of liquid release capability which may then outweigh the benefits provided by the gel in terms of increased moisture content. It is therefore preferred in some embodiments to provide inventive preparations without the addition of a film-forming substance.

In a specially preferred embodiment, the film forming substance of the present invention is a hyetellose, hypromellose, hyaluronate, polyvinylalcohol or polyvinylpyrrolidone. A particular preferred film-forming substance is polyvinylpyrrolidone (PVP).

It is presently believed that the film forming substance can be incorporated into the liposome or the liposome structure as well as be present at or near the surface of the liposomes.

The film forming substance applied in the present invention is present in the range between 0.1% to 10%, preferably between 0.5% and 7%, more preferably between 1% and 5%, most preferably between 2% and 4%, based on the total weight of the preparation.

In other preferred embodiments of the invention the preparation further comprises an active agent, in particular an anti-inflammatory agent.

Anti-inflammatory agents in accordance with the present invention broadly include antibiotic and antiviral preparations, and more specifically comprise antiseptic agents, antibiotic agents, corticosteroids and the like. Antiseptic agents are preferred.

In the context of this invention antiseptic agents are understood to include those disinfecting agents which are pharmaceutically acceptable and suitable for the intended treatment.

Preferred antiseptic agents comprise oxygen- and halogen-releasing compounds, preferably iodine and iodine complexes, and/or metal compounds, preferably silver- and mercury-compounds.

Further antiseptic compounds comprise organic disinfectants, including formaldehyde-releasing compounds, phenolic compounds including alkyl- and aryl-phenolic compounds, chinolines and acridines, hexahydropyrimidines, quartenary ammonia compounds, imines and salts thereof and guanidines.

It may be advantageous to include actives, such as disinfectants and anti-septics, at lower contents than in the prior art. Where the liquid level adjustment and control performance of the inventive preparations are more important than anti-infective aspects, the actives may advantageously be provided at concentrations only up to 90%, only up to 75%, sometimes only up to 50% and in some preferred embodiments only up to 25% of the concentrations known e.g. from comparable preparations in EP 0 639 373 (while in all these cases the concentration is non-zero and preferably at least 5%, more often at least 10% of those known from EP 0 639 373). This holds for inventive preparations containing liposomes, but also for such that do not contain liposomes (or other particulate carrier materials).

While EP 0 639 373 uses PVP-iodine as a preferred active agent other active agents other than PVP-iodine are used in specific preferred embodiments of the present invention.

If the preparation comprises liposomes, the active agent, preferably antiseptic agent, is often associated with the liposomes.

Since, however, in some cases the addition of particulate carriers, film-forming substances, active agents or combinations thereof may cause some loss of liquid release capability, it is specifically preferred in other embodiments, to omit either one of these ingredients particulate carriers, film-forming substances, active agents or combinations thereof.

A specifically preferred embodiment provides a preparations according to the invention which do not contain liposomes. In some specifically preferred embodiments, the inventive preparation is free of particulate carriers.

In a particularly preferred embodiment of the invention, the preparation does not contain iodine as active agent. In another preferred embodiment, the preparation is free of antiseptic agents. In still another preferred embodiment, the preparation according to the invention is free of anti-inflammatory agents. In still further preferred embodiments, the inventive preparations are free of active agents.

In another preferred embodiment, the preparation according to the invention is free of film-forming substances.

Free of antiseptic agent, in the context of the present invention, means that the preparation does not comprise oxygen- and halogen-releasing compounds, preferably iodine and iodine complexes, and/or metal compounds, preferably silver- and mercury-compounds, organic disinfectants, including formaldehyde-releasing compounds, phenolic compounds including alkyl- and aryl-phenolic compounds, chinolines and acridines, hexahydropyrimidines, quartenary ammonia compounds, imines and salts thereof and guanidines.

Free of anti-inflammatory agents means that the inventive preparation does not contain antibiotic and antiviral preparations, antibiotic agents or corticosteroids.

Free of active pharmaceutically agents in the context of this invention means that the inventive preparation does not contain any pharmaceutically active agents. The hydrogel itself is not covered by the term pharmaceutically active agent.

Free of particulate carrier means that the inventive preparation does not contain particulate carriers, especially not liposomes, microspheres, nanoparticles, or large porous particles Free of film-forming substances means that the inventive preparation does not contain film-forming substances, especially not hyetellose, hypromellose, hyaluronate, polyvinylalcohol or polyvinylpyrrolidone.

The preparation according to the invention may comprise further additives and adjuvants such as conserving agents, antioxidants, consistency forming additives or pH-adjusting agents.

The preparations according to the invention can optionally comprise wound healing agents. Suitable wound healing agents comprise e.g. dexpanthenol, allantoines, azulenes, tannins, vitamins (preferably vitamin B), and derivatives thereof.

The preparations according to the invention are capable of maintaining a level of moisture/liquid within the wound to an extent that wound healing is enhanced.

The level of moisture which an inventive preparation is capable to maintain in a wound can generally be measured by the capability to absorb a certain amount of liquid or to the ability to release liquid to a substrate and/or wound. The liquid release properties of the preparations according to the invention are of particular interest in the context of the present invention.

To determine the so-called "liquid affinity" of hydrogels, standard procedures are known to a person skilled in the art. A preferred test follows European norm EN 13726-1:2002. By this, the capability of hydrogels, in particular amorphous hydrogels, to release a liquid to gelatine or to absorb liquid from agar are measured. If necessary, the conditions of the test are adapted for the intended use.

The liquid affinity of hydrogel dressings is specified as the percentage of the capability to absorb or release liquids determined by the increase or decrease, respectively in gel weight.

The preparations according to the invention have been proven to be particularly suitable to release liquid or moisture, to wounds as well as test substrates. In preferred embodiments the preparation releases at least 8%, preferably at least 10%, more preferably at least 12%, at least 14%, at least 16%, at least 18%, at least 20% or most preferably at least 25% of the liquid from the test substrate under the test conditions of EN 13726-1:2002.

In preferred embodiments the liquid absorption, measured in gain of gel weight, is less than 15%, preferably less than 12%, more preferably less than 10%, less than 8%, less than 6%, less than 5% and most preferably less than 4%.

It is apparent that the preparations according to the invention may be designed to provide varying liquid absorption and release properties, and that for this purpose, all combinations of values given in above ranges may be selected.

The liquid affinity of hydrogel dressings can be classified according to the percentage of the absorption or release of liquid.

A wound dressing which absorbs 0 to 10% of its weight from Agar is classified as "type 1", greater than 10 to 20% as "type 2", greater than 20 to 30% as "type 3", greater than 30 to 40% as "type 4" and greater than 40 to 50% as "type 5", respectively.

The liquid affinity with respect to the liquid release to gelatine, which is measured by the decrease of the gel weight, is classified as follows: a liquid release in the range of 0 to 5% as "type a", greater than 5% to 10% as "type b", greater than 10% to 15% as "type c", greater than 15% to 20% as "type d", greater than 20% to 25% as "type e".

Correspondingly, a wound dressing that absorbs about 25% liquid, based on the original weight of the gel, from agar and hardly releases any liquid (less than 5%) to gelatine is classified as a "3a type" wound dressing.

In particularly preferred embodiments of the invention the preparation is classified as "type 1c", "type 1d", "type 1e" or "type 2e".

In a preferred embodiment the preparation according to the invention can applied in pre-gel form at the desired locus, e.g. as a liquid. The liquid preparation can easily be applied e.g. in form of a spray.

Such a liquid preparation can comprise water and/or any pharmaceutically acceptable solvent or any mixture of pharmaceutically acceptable solvents and water (water, as used anywhere in this specification includes all kinds of aqueous systems, like buffer solutions and the like). Preferably the pharmaceutically acceptable solvent(s) comprises one or more organic solvent(s). Volatile alcohol(s) are particularly preferred. Such alcohols are e.g. ethanol, n-propanol, i-proponal, and/or butanols and combinations of the afore-mentioned. After the preparation is applied at the intended locus, the hydrogel is formed by evaporation of one or more volatile solvent(s) or by absorption of the liquid component by body tissue.

Upon application of the pre-gel forming preparation at least one of the volatile components evaporates or is absorbed and forms gel preparations according to the invention.

Suitable pre-gels are e.g. disclosed in EP 0 704 206 which is herein incorporated by reference.

In general, the inventive preparations can be prepared by dispersing the gel-forming polymer in an amount of a suitable liquid or solvent, preferably water. The preparations according to the invention comprise between about 0.1 g and about 10 g, preferably between about 0.5 g and about 5 g, more preferably between about 1.0 g and about 3.0 g gel-forming polymer per 100 g preparation. The pH of the mixture can be adjusted by addition of a suitable acid or base, which are preferably added in solution, if necessary. The pH of the final preparation is between about 3 and about 7, preferably between about 4 and about 6.5, more preferably between about 5 and about 6. If the desired conditions (pH-value, etc.) are met, the gel is allowed to swell for an appropriate period of time.

In those preferred embodiments, wherein the preparation further comprises liposomes, the inventive preparations can be prepared by combining a suitable gel with liposomes or a liposomal preparation. The liposomal preparation can be prepared by any method known to a person skilled in the art. Suitable methods are e.g. disclosed in EP 0 639 373. If desired, elevated temperatures can be applied to facilitate the formation of the liposomal preparation. In preferred embodiments of the invention, the liposomal preparation is in the range of 0.1% to 30%, preferably in the range of 1% to 20%, even more preferably between 2% and 20%, based on the total weight of the preparation.

The liposomal preparation and the gel can be combined and homogenized, if necessary, to form a preparation according to the invention.

The person skilled in the art is well aware that further additives and adjuvants like conserving agents can be added to the inventive preparations at a time suitable to achieve preparations for the intended use. The skilled person also knows how to further process the inventive preparations in the production of pharmaceutical preparations, as necessary.

In case the specifically preferred embodiment further comprises at least one film-forming substance, the film-forming substance can be present in the range between 0.1 g to 10 g, preferably between 0.5 g and 7 g, more preferably between 1 g and 5 g, most preferably between 2 g and 4 g, based on 100 g of the preparation.

The film-forming substance is generally provided in solution, but can also be provided in any other suitable form known to the person skilled in the art. In a specifically preferred embodiment, the film-forming substance is at first combined with the liposomal preparation and subsequently added to the formed gel. The resulting mixture can then be further processed, as necessary.

In some preferred embodiments, an active agent, in particular an anti-inflammatory agent is comprised by the inventive preparation. In some specific embodiments, it is advantageous to provide the active agent at concentrations which are lower than in the prior art. The concentration of the active agent is, however, adjusted for the intended use of the inventive preparations. Some specifically preferred embodiments of the present invention comprise other active agents than PVP-iodine.

The active agent may be in a suitable form for combination with the liposomal preparation. In general, the combined mixture is subsequently added to the formed gel and can further be processed to form a preparation according to the invention.

In case the inventive preparation comprises further ingredients or adjuvants like conservatives, buffer solutions, etc., the skilled person is able to select and incorporate these substances into the preparations according to the invention for the intended use.

Specific inventive formulations are notable from the embodiment examples.

EMBODIMENT EXAMPLES

The features and advantages of this invention will become clear in more detail from the ensuing description of preferred embodiments. In the embodiments, which include an active agent, povidone iodine is exemplified and liposomes are chosen as the carrier. However, the povione iodine can be omitted to provide embodiments of the present invention which do not comprise an active agent, in particular any antiseptic agent. It is apparent for a person skilled in the art that PVP-iodine can be substituted by another active agent, suitable for the intended use. Likewise, the exemplified embodiments serve to illustrate mutatis mutandis, the characteristics of inventive preparations which comprise neither actives nor particulate carrier materials.

According to the invention, particulate carriers such as "large porous particles" or other micelles, nanoparticles, etc. instead of the exemplified liposomes, can be formulated with active agents like PVP-iodine.

Embodiment Example I

A Carbopol 980 NF composition was prepared. The amounts shown in Table I were used either for analytical or scale up compositions.

TABLE I

| Pos. | Substance | Amount (g/100 g) | Scale up (kg/1000 kg) |
|---|---|---|---|
| A | $H_2O$ | 90.00 | 900.00 |
| A | Carbopol ® 980 NF | 1.50 | 15.00 |
| B | $H_2O$ | 4.60 | 46.00 |
| B | NaOH solid | 0.46 | 4.6 |
| C | $H_2O$ | ad 100 | ad 1000 |

Pos. stands for Position (see also below Table II).
Carbopol 980 NF was purchased from BF Goodrich or Noveon.

In Table II, column 2 the exact order of steps and the parameters of each step are given. All steps were performed at room temperature except where indicated otherwise. All substances were of a purity grade common for pharmaceutical preparations.

TABLE II

| No. | |
|---|---|
| 1 | Carefully add Carbopol of Pos. A to water of Pos. A, which is provided in a beaker<br>Disperse by stirring (approx. 305 upm) for about 30 min<br>Stir until no inhomogeneities are visible<br>Determine pH |
| 2 | Provide water of Pos. B in a separate beaker and dissolve NaOH of Pos. B by stirring |
| 3 | Adjust pH of product of step 1 with NaOH solution to 5.5<br>Stir for 3 min after each addition of NaOH at about 350 upm<br>Stir for at least 10 min at about 350 upm<br>Allow gel to swell |

Embodiment Example II

Formulation with Buffer and Germall II

A Carbopol 980NF composition was prepared. The amounts shown in Table III were used either for analytical or scale up compositions.

TABLE III

| Pos. | Substance | Amount (g/100 g) | Scale up (kg/5000 kg) |
|---|---|---|---|
| A | $H_2O$ | 40.00 | 2000 |
| A | Germall II | 0.30 | 15.00 |
| B | Carbopol 980 NF | 1.50 | 75.0 |
| C | $H_2O$ | 4.60 | 230.00 |
| C | NaOH solid | 0.46 | 23.00 |
| D | $H_2O$ | 48.00 | 2400 |
| E | $H_2O$ | 3.00 | 150 |
| E | $Na_2(HPO_4)$ | 0.225 | 11.25 |
| E | Citric acid | 0.1065 | 5.33 |
| F | $H_2O$ | ad 100 | ad 5000 |

Pos. stands for Position (see also below Table IV).
Carbopol 980NF was purchased from BF Goodrich.

In Table IV, column 2 the exact order of steps and the parameters of each step are given. All steps were performed at room temperature except where indicated otherwise. All substances were of a purity grade common for pharmaceutical preparations.

TABLE IV

| No. | |
|---|---|
| 1 | Germall II of Pos. A is carefully added to water of Pos. A into an Unimax LM5<br>Dissolve Germall II by stirring at 100 upm (units per minute) |
| 2 | Carefully add Carbopol 980 NF of Pos. B<br>Disperse by stirring (approx. 100 upm) for about 30 min<br>Break up agglomerates, if necessary<br>Subsequent homogenization is performed until no inhomogeneities are visible<br>Let gel swell for at least 16 hours |
| 3 | Provide water of Pos. C in a beaker and dissolve NaOH of Pos. C by stirring |
| 4 | Adjust pH of gel of step 2 with NaOH solution to 3 (+/−0.2)<br>Addition can be performed into an open Unimix mixer<br>Stir for 10 min after each addition |
| 5 | Water of Pos. D is pumped via cap valve into Unimax LM5 and stirred for 10 min (100 upm)<br>Subsequent homogenization is performed for 2 min at 8500 upm |

TABLE IV-continued

| No. | |
|---|---|
| 6 | Adjust pH of gel by addition of NaOH solution to 5.5 (+/−0.2) Addition can be performed into an open Unimix LM 5 Rinse circulation pump lines by homogenization and subsequent stirring for 10 min Adjust pH, if necessary |
| 7 | Warm water of Pos. E to 40° C. and dissolve salts of Pos. E ($Na_2(HPO_4)$ and citric acid) while stirring Let cool to ≤30° C. while stirring |
| 8 | Add buffer solution to gel and stir for 10 min |
| 9 | Determine and add residual amount of water (calculate 5000 sum of all ingredients) Stir for 10 min Rinse circulation pump lines by homogenization |

Embodiment Example III

+Germall II

A liposomal Carbopol 980NF composition was prepared. The amounts shown in Table V were used either for analytical or scale up compositions.

TABLE V

| Pos. | Substance | Amount (g/100 g) | Scale up (kg/5000 kg) |
|---|---|---|---|
| A | $H_2O$ | 40.00 | 2000 |
| A | Germall II | 0.30 | 15.00 |
| B | Carbopol 980NF | 1.50 | 75.0 |
| C | $H_2O$ | 4.60 | 230.0 |
| C | NaOH solid | 0.46 | 23.00 |
| D | $H_2O$ | 15.00 | 750 |
| D | Phospholipon 90 H | 3.00 | 150 |
| E | $H_2O$ | 27.50 | 1375 |
| F | $H_2O$ | 2.50 | 125 |
| G | $H_2O$ | 3.00 | 150 |
| G | $Na_2(HPO_4)$ | 0.225 | 11.25 |
| G | Citric acid | 0.1065 | 5.33 |
| H | $H_2O$ | Ad 100 | ad 5000 |

Pos. stands for Position (see also below Table V).
Carbopol 980NF was purchased from BF Goodrich.
Phospholipon 90 H was purchased from Rhone Poulene.

In Table VI, column 2 the exact order of steps and the parameters of each step are given. All steps were performed at room temperature except where indicated otherwise. All substances were of a purity grade common for pharmaceutical preparations.

TABLE VI

| No. | |
|---|---|
| 1 | Germall II of Pos. A is carefully added to water of Pos. A into an Unimax LM 5 Dissolve Germall II by stirring at 100 upm (units per minute) |
| 2 | Carefully add Carbopol 980NF of Pos. B Disperse by stirring (approx. 100 upm) for about 30 min Break up agglomerates, if necessary Subsequent homogenization is performed until no inhomogeneities are visible Let gel swell for at least 16 hours |
| 3 | Provide water of Pos. C in a beaker and dissolve solid NaOH of Pos. C by stirring while heating to 65° C. Add Phospholipon of Pos. D carefully and stir for 60 min (450 upm) at 65° C. |
| 4 | Cool dispersion of step 3 while stirring (100 upm) to 30° C. (water bath) and compensate water loss, if necessary |
| 5 | Provide water of Pos. C in a beaker and dissolve NaOH of Pos. C by stirring |

TABLE VI-continued

| No. | |
|---|---|
| 6 | Adjust pH of gel of step 2 by addition of NaOH solution to 3.0 (+/−0.2) Addition can be performed into an open Unimix LM 5 Stir for 10 min after each addition |
| 7 | Add water of Pos. E to liposomal dispersion of step 4 while stirring and stir for additional 10 min |
| 8 | Liposomal dispersion is pumped via cap valve into Unimix LM5 and stirred for 10 min at 100 upm Rinse beaker with water of Pos. F and add to preparation Subsequent homogenization is performed for 2 min at 8500 upm |
| 9 | Adjust pH of gel by addition of NaOH solution to 5.5 (+/−0.2) Addition can be performed into an open Unimix LM 5 Stir for 10 min after each addition Rinse circulation pump lines by homogenization and stir for at least 10 min Adjust pH, if necessary |
| 10 | Warm water of Pos. E to 40° C. and dissolve salts of Pos. E ($Na_2(HPO_4)$ and citric acid) by stirring Let cool to ≤30° C. while stirring |
| 11 | Add buffer solution to gel and stir for 10 min |
| 12 | Determine and add residual amount of water (calculate 5000 sum of all ingredients), stir for 10 min, Rinse circulation pump lines by homogenization |

Embodiment Example IV

A liposomal Carbopol 980NF composition was prepared. The amounts shown in Table VII were used either for analytical or scale up compositions.

TABLE VII

| Pos. | Substance | Amount (g/100 g) | Scale up (kg/5000 kg) |
|---|---|---|---|
| A | $H_2O$ | 40.00 | 2000 |
| A | Germall II | 0.30 | 15.00 |
| B | Carbopol 980NF | 1.50 | 75.0 |
| C | $H_2O$ | 4.60 | 230.0 |
| C | NaOH solid | 0.46 | 23.0 |
| D | $H_2O$ | 15.00 | 750 |
| D | Phospholipon 90 H | 3.00 | 150 |
| E | $H_2O$ | 22.00 | 1100 |
| E | PVP (Kollidon 30) | 3.00 | 150 |
| F | $H_2O$ | 2.50 | 125 |
| G | $H_2O$ | 2.50 | 125 |
| H | $H_2O$ | 3.00 | 150 |
| H | $Na_2(HPO_4)$ | 0.225 | 11.25 |
| G | Citric acid | 0.1065 | 5.33 |
| I | $H_2O$ | Ad 100 | ad 5000 |

Pos. stands for Position (see also below Table VIII).
Carbopol 980NF was purchased from BF Goodrich,
Phospholipon 90 H was purchased from Rhone Poulene and
PVP (Kollidon 30) from BASF.

In Table VIII, column 2 the exact order of steps and the parameters of each step are given. All steps were performed at room temperature except where indicated otherwise. All substances were of a purity grade common for pharmaceutical preparations.

TABLE VIII

| No. | |
|---|---|
| 1 | Germall II of Pos. A is carefully added to water of Pos. A in an Unimix LM 5 Dissolve Germall II by stirring at approx. 100 upm (units per minute) |
| 2 | Carefully add Carbopol 980NF of Pos. B Disperse by stirring (approx. 100 upm) for about 30 min Break up agglomerates, if necessary Subsequent homogenization is performed until no |

TABLE VIII-continued

| No. | |
|---|---|
| | inhomogeneities are visible |
| | Let gel swell for at least 16 hours |
| 3 | Provide water of Pos. D in a beaker and dissolve solid NaOH of Pos. C by stirring while heating to 65° C. Add Phospholipon of Pos. D and stir at 65° C. for 60 min (450 upm) |
| 4 | Cool dispersion of step 3 while stirring (100 upm) to 30° C. (water bath) and compensate water loss, if necessary |
| 5 | Provide water of Pos. C in a beaker and dissolve NaOH of Pos. C by stirring |
| 6 | Adjust pH of gel of step 2 by addition of NaOH solution to 3.0 (+/−0.2) Addition can be performed into an open Unimix LM5 Stir for 10 min after each addition |
| 7 | Water of Pos. E is provided in a beaker and PVP of Pos. E is carefully added while stirring. Stir for 30 min at 450 upm |
| 8 | Add PVP of step 7 to liposomal dispersion of step 4 and stir for 10 min. Rinse beaker with water of Pos. F and add to preparation |
| 9 | Liposomal dispersion is pumped via cap valve into Unimix LM5 and stirred for 10 min at 100 upm Rinse beaker with water of Pos. G and add to preparation Subsequent homogenization is performed for 2 min at 8500 upm |
| 10 | Adjust pH of gel by addition of NaOH solution to 5.5 (+/−0.2) Addition can be performed into an open Unimix LM5 Stir for 10 min after each addition Rinse circulation pump lines by homogenization and stir for at least 10 min Adjust pH, if necessary |
| 11 | Warm water of Pos. H to 40° C. and dissolve salts of Pos. H ($Na_2(HPO_4)$ and citric acid) by stirring Let cool to ≤30° C. while stirring |
| 12 | Add buffer solution to gel and stir for 10 min |
| 13 | Determine and add residual amount (calculate 5000 sum of all ingredients), stir for at least 10 min, |

Embodiment Example V

A liposomal composition containing PVP-iodine as an active agent was prepared. The amounts shown in Table IX were used either for analytical or scale up compositions.

TABLE IX

| Pos. | Substance | Amount (g/100 g) | Scale up (kg/1500 kg) |
|---|---|---|---|
| A | $H_2O$ | 15.0 | 200.0 |
| A | Phospolipon 90 H | 3.0 | 45.0 |
| B | $H_2O$ | 40.0 | 600.0 |
| B | Carbopol ® 980 NF | 1.5 | 22.5 |
| C | $H_2O$ | 2.0 | 30.0 |
| C | $KIO_3$ | 0.0708 | 1.09 |
| D | $H_2O$ | 20.0 | 300.0 |
| D | PVP-iodine 30/06 Available iodine (10%) | 3.0 | 45.0 |
| E | $H_2O$ | 2.5 | 50.0 |
| F | $H_2O$ | 2.5 | 50.0 |
| G | $H_2O$ | 4.6 | 69.0 |
| G | NaOH solid | 0.46 | 6.9 |
| I | Citric acid, $H_2O$ free | 0.1065 | 1.059 |
| I | $Na_2(HPO_4)$, $H_2O$ free | 0.225 | 3.37 |
| I | $H_2O$ | 3.0 | 45.0 |
| H | $H_2O$ | Ad 100.0 | ad 1500 |

Pos. stands for Position (see also below Table X).
Phospholipon ® 90 H was purchased from Aventis (Germany).
Carbopol ® 980 NF was purchased from Noveon Inc. (USA) or Gattefossé (Germany) and PVP Iodine 30/06 was purchased from BASF (Germany).

In Table X, column 2 the exact order of steps and the parameters of each step are given. Column 3 discusses non-exclusive alternatives. All steps were performed at room temperature except where indicated otherwise. All substances were of a purity grade common for pharmaceutical preparations.

TABLE X

| No. | Embodiment example VII | Alternatives |
|---|---|---|
| 1 | Carbopol 980 NF is mixed into $H_2O$ without agglomeration (Pos. B). Stirring for 30 min at approx. 30 upm (units per minute) in conventional stirrer. Visual control for Polyacrylic acid-agglomerates. If necessary, homogenize gel in conventional homogenisator for 2 min at 3000 upm. Subsequently stir gel for 30 min at 30 upm in conventional stirrer. Eventually control again for Polyacrylicacid-agglomerates. If present, remove them and stir again for 15 min at 30 upm. Eventually homogenize again. Let gel swell for at least 14 h. | Substances: Other gel-forming substances may be used. Homogenization time can vary: shorten to 1 min prolong to 10 min (caution! gel structure may be destroyed) Stirring time can be altered as desired. Only condition is that gel is free of agglomerates at the end. Swelling time may be altered from 15 min to 5 days. Preferably the gel has formed before other substances are added. Adjustment of pH to 2-8 may be performed at this stage. Adjustment to pH 3-6 is preferred. |
| 2 | Dissolve $H_2O$ and $KIO_3$ completely in a suitable vessel (Pos. C). Alternatively a 30-40% $KIO_3$ solution may be used. | $H_2O$-temperature may be adjusted to anywhere between ambient temperature and 100° C. $KIO_3$ is not obligatory. |
| 3 | Dissolve NaOH completely in $H_2O$ (Pos. G). | NaOH is used in concentrations common for pharmaceutical preparations. Other Bases or substances suggested by the supplier of the gel forming substances may also be used for formation of gel structure as e.g. KOH, Triethanol-amine, 2-Amino-2-methyl-1-propanol, tris(hydroacnemethyl)aminoethan, 2-hydroacnepropyl-ethylen-diamine, diisopropanolamine. |

TABLE X-continued

| No. | Embodiment example VII | Alternatives |
|---|---|---|
| 4 | Mix PVP-iodine into $H_2O$ while stirring at 1000 upm in conventional stirrer (Pos. D). Stir mixture for futher 60-70 min at 1000 upm until it is completely dissolved. | Stirring time and speed can be altered arbitrarily. Important: PVP-Iodine has to be dissolved completely. |
| 5 | Warm $H_2O$ to 65° C. while stirring with 1000 upm in conventional stirrer. Then add slowly Phospholipon ® 90 H (Pos. A). Take care that no agglomerates are formed. Stir dispersion for further 90 min at 65° C.-70° C. and 1000 upm. Subsequently cool liposomal dispersion to ≤30° C. while stirring at 500 upm | Possible temperature range: 40° C.-120° C. 50° C.-75° C. is preferred because of phase transition temperature. Other liposome-forming materials or mixtures thereof may be used. Stirring time and speed: Is dependent on equipment. A complete dispersion has to be achieved. Apparatus of the rotor/stator principle, high pressure homogenisators, ultrasound or extrusion technology may also be used for stirring. |
| 6 | By adding the NaOH-solution (No. 3) the gel is adjusted to a pH of 3.0 (±0.2). | Further processing to a gel may be feasible without pH pre-adjustment and is dependent on the gel-forming substance |
| 7 | The $KIO_3$ solution (No. 2) is added to the PVP-Iodine solution (No. 4) while stirring at 1000 upm. Stirring continued for at least 60 min. | Reaction between $KIO_3$ and PVP-iodine is time dependent. To ensure a complete reaction, the stirring time has to be adapted accordingly. Thus, stirring time may be between 10 min and 2 h |
| 8 | The PVP-iodine-$KIO_3$-solution is pumped into the liposomal dispersion (No. 5). Subsequently it is stirred for 30 min at 1000 upm. | Stirring time is variable depending on until when an homogeneous mixture has formed. |
| 9 | The PVP-iodine-$KIO_3$-liposomes-dispesion is added to the gel (No. 6). It is stirred for 30 min at 30 upm. Subsequently homogenization is performed by forced circulation pumping for 2 min at 2800 upm. After checking for agglomerates, it may be homogenized for further 1-2 min. | Stirring time is variable depending on until when an homogeneous mixture has formed. Stirring time should be as short as possible so that gel structure gets not disrupted. |
| 10 | Remove agglomerates if present. Add 50.0 kg NaOH-solution (in the scale up, point 3) while stirring at 30 upm. Stir for further 30 min at 30 upm at ≤30° C. Cool if necessary. Determine pH and add additional NaOH until an pH of 5.5 (±0.2) is achieved. After each adding step stir for 20 min. After each adding step homogenize by circulation pressure pumping for 15 sec at 1000 upm. After adjustment of pH stir for further 15 min at 30 upm. Check pH and correct if necessary. After successful pH adjustment add remaining $H_2O$ amount which depends on the amount of NaOH used. | Adjust stirring time and speed to gel quality. Amounts of NaOH may vary. Adding of base by step wise adjustment until desired pH is achieved. |
| 11 | Mix buffer solution at 30° C. while stirring until it is completely dissolved (Pos. I). | Temperature can be raised to 40° C. Other suitable buffers may also be used. |
| 12 | Buffer solution is added to the product (No. 10) while stirring for 15 min at 30 upm. Degas by application of vacuum. | The desired product quality (storage stability) is achieved by addition of the buffer. Stirring time is variable depending on until when an homogeneous mixture has formed. Degasing may be achieved by other means than vacuum. |

TABLE X-continued

| No. | Embodiment example VII | Alternatives |
|---|---|---|
| 13 | Add the remaining H$_2$O-amount (Pos. H) and stir for 30 min at 25 upm Optionally homogenization may be performed by circulation pressure pumping for 15 sec at 1000 upm. Stir for another 30 min. Check visually for agglomerates | Stirring time is variable depending on until when an homogeneous mixture has formed. |

Positions E and F of Table IX are used for washing the KIO$_3$- and the PVP-iodine vessels (points 2 and 4 of Table X).

Determination of the Liquid Affinity

The test procedures of he European norm EN 13726-1: 2002, in particular the German version EN 13726-1:2002 (D), were followed if not stated otherwise.

The determination of the liquid affinity of the inventive preparations and reference products was conducted in a sealed laboratory at temperatures of 25 (±2° C. and 38% relative humidity.

Agar and gelatine which are used as test substrates were purchased from Merck.

The tests were performed according to test procedures for primary wound dressings.

The following embodiments were tested:

a) Carbopol® 980 NF Gel b) Liposomal Carbopol® 980 NF Gel c) Liposomal Carbopol® 980 NF Gel and PVP The capability of the inventive preparations to absorb and release liquid to the test substrate was determined as a percentage of weight gain or weight loss of the samples. The results of the examples a) to c) are shown in Tables XI to XIII.

For the embodiment examples a) to c) as well as the comparative examples d) to g) measurements of the liquid absorption and liquid release capability were conducted. Five measurements each, numbered samples 1 to 5 within each example (embodiment and comparative examples) were performed (for the embodiment examples see Table XI to XIII and for comparative examples see Tables XIV to XVI). The mean of these five measurements as well as the standard deviation were determined and referred to within the further discussion.

TABLE XI

Liquid affinity of Carbopol ® 980 NF Gel (a):

| Sample | Agar (absorption) liquid affinity gain of gel weight (%) | Gelatine (release) liquid affinity loss of gel weight (%) |
|---|---|---|
| 1 | 4 | −18 |
| 2 | 4 | −18 |
| 3 | 4 | −18 |
| 4 | 4 | −18 |
| 5 | 4 | −19 |
| Mean | 4 | −18 |
| S$_{rel}$ | 0% | 2.5% |

The inventive Carbopol® 980 NF gel (a) releases liquid very well, which is demonstrated by 18% loss of gel weight. The inventive gel exhibits a liquid absorption of 4%. The Carbopol® 980 NF gel a) is a "type 1d" gel by the standards of EN13726-1:2002.

TABLE XII

Liquid affinity of liposomal Carbopol ® 980 NF Gel (b):

| Sample | Agar (absorption) liquid affinity gain of gel weight (%) | Gelatine (release) liquid affinity loss of gel weight (%) |
|---|---|---|
| 1 | 5 | −17 |
| 2 | 5 | −17 |
| 3 | 5 | −17 |
| 4 | 5 | −17 |
| 5 | 5 | −18 |
| Mean | 5 | −17 |
| S$_{rel}$ | 0% | 2.6% |

The liposomal Carbopol® NF980 gel (b) reveals good liquid release properties, which are at 17% weight loss, only slightly lower than those of Carbopol® 980 NF preparation a). The liquid absorption capacity is slightly increased in comparison to a) (see Table XI) and revealed 5% liquid absorption. The liposomal gel preparation b) can be classified as a "type 1 d" by the standards of EN 13726-1:2002.

TABLE XIII

Liquid affinity of liposomal Carbopol ® 980 NF Gel and PVP (c):

| Sample | Agar (absorption) liquid affinity gain of gel weight (%) | Gelatine (release) liquid affinity loss of gel weight (%) |
|---|---|---|
| 1 | 9 | −14 |
| 2 | 9 | −14 |
| 3 | 8 | −14 |
| 4 | 9 | −14 |
| 5 | 8 | −14 |
| Mean | 9 | −14 |
| S$_{rel}$ | 6.4% | 0% |

The liquid release properties of the inventive liposomal gel (c) including PVP as a film-forming substance reveals a liquid release value of 14% and an absorption capacity of 9%. The liposomal Carbopol® 980 NF Gel including PVP is a "type 1c" by the standards of EN13726-1:2002.

By comparison, four commercially available gel preparations were tested with respect to their liquid affinity:

d) Askina® Gel (available from Braun)

e) IntraSite® Gel (available from Smith & Nephew)

f) NU-Gel (available from Johnson & Johnson)

g) Varihesive® Hydrogel (available from convaTec)

The results of the liquid affinity of the comparative preparations are shown in Tables XIV to XVII.

TABLE XIV

Liquid affinity of Askina ® Gel (d):

| Sample | Agar (absorption) liquid affinity gain of gel weight (%) | Gelatine (release) liquid affinity loss of gel weight (%) |
|---|---|---|
| 1 | 28 | −4* |
| 2 | 28 | −3 |
| 3 | 28 | −3 |
| 4 | 29 | −3 |
| 5 | 28 | −4 |
| Mean | 28 | −3 |
| $S_{rel}$ | 1.6% | 15.4% |

*Sample has not been used for further analysis (film broke)

The Askina® Gel exhibits an liquid release of 3%, which is significantly lower than in the examples a) to c) (see Tables XI to XIII). The liquid absorption is with 28% higher than in the examples a) to c). Askina® Gel is classified as a "type 3a" by the standards of EN13726-1:2002.

TABLE XV

Liquid affinity of IntraSite ® Gel (e)

| Sample | Agar (absorption) liquid affinity gain of gel weight (%) | Gelatine (release) liquid affinity loss of gel weight (%) |
|---|---|---|
| 1 | 15 | −6 |
| 2 | 25 | −7 |
| 3 | 13 | −7 |
| 4 | 13 | −7 |
| 5 | 15 | −6 |
| Mean | 16 | −7 |
| $S_{rel}$ | 31% | 8.3% |

The IntraSite® Gel releases 7% of the liquid to the test substrate and showed a liquid absorption of 16%. The IntraSite® Gel has a lower liquid release capacity than the preparation according to the invention. IntraSite® Gel is classified as a "type 2b" by the standards of EN 13726-1:2002.

TABLE XVI

Liquid affinity of NU-Gel (f):

| Sample | Agar (absorption) liquid affinity gain of gel weight (%) | Gelatine (release) liquid affinity loss of gel weight (%) |
|---|---|---|
| 1 | 29 | −2 |
| 2 | 29 | −4* |
| 3 | 29 | −2 |
| 4 | 29 | −5* |
| 5 | 29 | −2 |
| Mean | 29 | −2 |
| $S_{rel}$ | 0% | 0% |

*Sample has not been used for further analysis (film broke)

The NU Gel exhibits only a very low liquid release of 2%, while its liquid absorption is determined to be 29%. NU Gel is classified as a "type 3a" by the standards of EN13726-1:2002.

TABLE XVII

Liquid affinity of Varihesive ® Hydrogel (g):

| Sample | Agar (absorption) liquid affinity gain of gel weight (%) | Gelatine (release) liquid affinity loss of gel weight (%) |
|---|---|---|
| 1 | 32 | −6 |
| 2 | 32 | −6 |
| 3 | 32 | −6 |
| 4 | 32 | −6 |
| 5 | 32 | −6 |
| Mean | 32 | −6 |
| $S_{rel}$ | 0% | 0% |

The Varihesive® Hydrogel revealed a liquid release value of 6%, which is significantly lower than the release capacity of the inventive preparations. The liquid absorption is 32%. Varihesive® Hydrogel is classified as a "4b type" by the standards of EN 13726-1:2002.

The liquid affinity tests clearly demonstrates that the liquid release properties of the preparations according to the invention are significantly higher than the release characteristics of the known gels of the prior art.

The invention claimed is:

1. A preparation for wound healing comprising a hydrogel comprising 1-3% by weight of a USP Carbomer 940 series polymer and water, said hydrogel having a pH value in the range of 4 to 6.5, wherein the capability of the preparation to release liquid is greater than its capability to absorb liquid when applied to a wound, such that when tested in accordance with EN 13726-1:2002, the preparation has liquid release capability, measured by a decrease of hydrogel weight, of at least 12% and a liquid absorption capability, measured in gain of hydrogel weight, of less than 12%; the preparation does not contain iodine.

2. The preparation according to claim 1, wherein the preparation further comprises one or more additives selected from the group consisting of adjuvants, conserving agents, antioxidants, consistency forming additives and pH-adjusting agents.

3. The preparation according to claim 1, wherein the preparation absorbs liquid absorption of the hydrogel is less than 8% liquid, as tested in accordance with EN 13726-1:2002.

4. The preparation according to claim 1, wherein the preparation absorbs liquid absorption of the hydrogel is less than 15% liquid, as tested in accordance with EN 13726-1:2002.

5. A wound dressing comprising a preparation according to claim 1.

6. A method for treating a wound, wherein said method comprises administering, to the wound, a hydrogel preparation for wound healing according to claim 1 comprising a USP Carbomer 940 series; wherein the hydrogel has a pH value in the range of 4 to 6.5; the capability of the hydrogel to release liquid is greater than its capability to absorb liquid; and the hydrogel preparation does not include a liposome.

7. The preparation according to claim 1, further comprising at least one antiseptic agent.

8. The preparation according to claim 7, wherein the antiseptic agent comprises at least one compound selected from the group consisting of oxygen- and halogen-releasing compounds and metal compounds.

9. The preparation according to claim 1, further comprising liposomes.

10. The preparation according to claim 9, wherein the liposomes are phospholipid-based liposomes.

11. The preparation according to claim 1, further comprising a wound-healing promoting agent.

12. The preparation according to claim 1, wherein said preparation is free of liposomes.

13. The preparation according to claim 1, wherein the polymer is Carbopol 980NF.

14. The preparation according to claim 1, wherein the pH is in the range of 5 to 6.

15. A wound dressing comprising a hydrogel comprising 1-3% by weight of a USP Carbomer 940 series and water, said hydrogel having a pH value in the range of 4 to 6.5.

16. The wound dressing of claim 15, wherein the polymer is Carbopol 980NF.

17. The wound dressing according to claim 15, further comprising a film forming substance.

18. The wound dressing according to claim 15, further comprising at least one antiseptic agent.

19. The wound dressing according to claim 18, wherein the antiseptic agent comprises at least one compound selected from the group consisting of oxygen- and halogen-releasing compounds and metal compounds.

* * * * *